US007119051B2

(12) United States Patent
Farrell et al.

(10) Patent No.: US 7,119,051 B2
(45) Date of Patent: Oct. 10, 2006

(54) PROCESS FOR MAKING BAR COMPOSITION HAVING LITTLE OR NO EFFLORESCENCE

(75) Inventors: Terence James Farrell, Tenafly, NJ (US); Michael Irwin Hill, Mahwah, NJ (US)

(73) Assignee: Unilever Home & Personal Care, USA division of Conopco, Inc., Greenwich, CT (US)

( * ) Notice: Subject to any disclaimer, the term of this patent is extended or adjusted under 35 U.S.C. 154(b) by 151 days.

(21) Appl. No.: 11/007,842

(22) Filed: Dec. 9, 2004

(65) Prior Publication Data

US 2006/0128580 A1 Jun. 15, 2006

(51) Int. Cl.
*A61K 7/00* (2006.01)

(52) U.S. Cl. ...................... 510/141; 510/152; 510/153; 510/155; 510/450; 510/458

(58) Field of Classification Search ................ 510/141, 510/152, 153, 155, 458, 508
See application file for complete search history.

(56) References Cited

U.S. PATENT DOCUMENTS 6,207,636 B1 * 3/2001 Benjamin et al. ........... 510/458
6,218,348 B1 * 4/2001 Aronson et al. ............ 510/153
6,310,016 B1 * 10/2001 Behal et al. ................ 510/152

* cited by examiner

*Primary Examiner*—Necholus Ogden
(74) *Attorney, Agent, or Firm*—Ronald A. Koatz

(57) ABSTRACT

The invention relates to novel method of incorporating free fatty acid into soap-based bars to minimize or eliminate efflorescence and to compositions made by the process.

9 Claims, No Drawings

PROCESS FOR MAKING BAR COMPOSITION HAVING LITTLE OR NO EFFLORESCENCE

FIELD OF THE INVENTION

The invention relates to fatty acid soap bars additionally comprising certain organic fatty acid salts used as superfatting agents (e.g., citric acid, adipic acid, glycolic acid), which salts would normally cause such bars to strongly effloresce. Use of aluminum hydroxide in these bars in such compositions remarkably allows production of such "superfatted" bars (i.e., "superfat" refers to free fatty acid used); while significantly reducing or eliminating the efflorescence problem.

BACKGROUND OF THE INVENTION

It is desirable to "superfat" (add free fatty acid) to fatty acid soap bars because they provide a creamy, tactile feel desirable to many consumers.

One method of superfattying a bar is to simply add free fatty acid to soap. However, the addition of free fatty acid is generally more expensive than producing fatty acid in-situ via production of organic or inorganic acids from their counterpart salts. Also, when adding free fatty acid to soap the levels are limited (e.g., less than about 8% by wt. bar composition) because the free fatty acid may cause the bar to be tacky (sticky and prone to leaving residue when touched); may cause discoloration; and/or may reduce lather (see U.S. Pat. No. 6,218,348 to Aronson et al. (column 4)).

Another way of introducing free fatty acid into a soap bar is to form the free fatty acid directly in the reaction from the fatty acid soap (i.e., the "soap", which is a salt of fatty acid, is broken down to free fatty acid upon release of the counter electrolyte salt). Typically such a reaction may be precipitated by use of an acid (e.g., citric acid) whose pKa is less than that of the fatty acid soap. Because of its lower pKa, the acid will "attract" the electrolyte salt (e.g., sodium) from the fatty acid soap thereby forming free fatty acid and a salt of the protic acid used to cause the precipitation (e.g., sodium citrate in the case of citric acid addition).

One problem with this method of generating free fatty acid from the soap is that, as elevated levels of protic acid salts are produced (e.g., production of sodium citrate during the production of free fatty acid from the soap), efflorescence (i.e., the appearance of salt crystals which both provide a negative visual and tactile cue) can occur.

U.S. Pat. No. 6,218,348 to Aronson et al., for example, describes bars containing free fatty acids, polyalkylene glycol and specific salts of protic acid (i.e., salts having pKa less than 6; the lower the pKa, the stronger the acid) wherein said bars are said to have beneficial sensory properties and can improve skin. The patent, however, fails to recognize that the protic acid salts may cause efflorescence during the in situ production of fatty acid from the soap; and there is, of course, no discussion of how to deal with this issue.

One solution to the problem has been to partially generate free fatty acid (i.e., at a level that there is not enough salt formed to cause efflorescence) and then adding free fatty acid to make up the difference to a desired higher level where such efflorescence will normally have been detected. This method is quite costly.

Unexpectedly, applicants have found that when a sodium aluminate solution (precipitating aluminum hydroxide in final bar composition) is added during processing (e.g., to reverse titrate excess levels of free fatty acid generated by the use of protic acid having pKa lower than soap), the resulting generated aluminum hydroxide acts to hinder or eliminate altogether the efflorescence normally caused by production of the precipitated protic acid salt (e.g., sodium citrate).

The aluminate technology of reacting fatty acid or acid precursor and, for example, aluminum containing alkaline material (e.g., sodium aluminate) is not new. In U.S. Pat. No. 6,207,636 to Benjamin et al., for example, a low total fatty matter ((TFM); the term is used to denote % by wt. fatty acid and triglyceride residue percent, without taking into account accompanying cations) bar is prepared comprising 25 to 75% TFM, 9.0 to 16% colloidal aluminum hydroxide (A-gel), 12 to 52% water, optional benefit agent and conventional additives.

There is no disclosure, however, of soap/free fatty acid bars or of the use of protic acid having pKas lower than fatty acid in the fatty acid soap; and there is no disclosure of the use of such protic acids to produce free fatty acids from the soap. There is also, therefore, no teaching or disclosure of aluminate (and precipitated aluminum hydroxide) used to resolve the problem caused by protic acid salt precipitation.

Similarly, U.S. Pat. No. 6,310,011 to Behal discloses TFM bars comprising a colloidal aluminum hydroxide phosphate complex, but neither teaches nor suggest bars where both specific salts of protic acid (having pKa lower than the fatty acid soap) and aluminum hydroxide are found in the final bar, or that use of the hydroxide ameliorates the efflorescence problem caused by the protic acid salt generated even as free fatty acid is being produced from the fatty acid soap.

The present invention represents a novel marriage of the two technologies resulting in novel composition, novel processes to make the compositions as well as unexpected amelioration of the efflorescence problem.

BRIEF DESCRIPTION OF INVENTION

The present invention comprises novel bar compositions and novel processes for making them wherein the compositions comprise fatty acid soap, free fatty acid (prepared in excess during processing using certain organic protic acids with pKa lower than that of the fatty acid component of the fatty acid soap), protic acid salts (resulting from precipitation of protic acid and the electrolyte component of the original fatty acid salt before free fatty acid is generated), and aluminum hydroxide (resulting from use of sodium aluminate to titrate excess free fatty acid back to fatty acid soap).

More particularly, the final bar composition comprises:

(1) 25 to 85% by wt., preferably 30 to 75% by wt. fatty acid soap (0% to 10% by wt. optional surfactant may be used);

(2) 0 to 15%, preferably 0.5 to 10% by wt. $C_8$ to $C_{20}$ free fatty acid (e.g., some amount of free fatty acid will be produced from the fatty acid soap as component (3) salt reacts with the counterion of the fatty acid soap (1); however the free fatty acid can be removed by back titration using aluminate solution;

(3) 0.01 to 7%, preferably 0.05 to 6%, more preferably 0.1 to 5% by wt. organic protic acid salt (preferably salts of citric acid such as alkali metal citrates), wherein protic acid has pKa less than that of fatty acid component of fatty acid soap;

(4) 0.2 to 8%, preferably 0.5 to 2.5% by wt. aluminum hydroxide (formed when aluminate solution comprising water, alkali metal hydroxide and alumina back titrates free fatty acid to soap;

(5) 5 to 20%% by wt., preferably 6 to 18% water; and (6) 2 to 8% by wt. alkylene glycol (e.g., polyethylene glycol);

wherein said composition results in little or no efflorescence (measured via storage studies under varying conditions for at least 4 weeks);

By little or no efflorescence is meant that there is no visual crystalline formation and the bar is visually "smooth" rather than fuzzy. Typical storage conditions are at about 30° C. and relative humidity (RH) of 70% for four weeks.

The bars may optionally comprise other components conventionally found in bar compositions such as additional surfactants, fillers, perfumes, colorants, etc.

In a second aspect, the invention comprises a process for making compositions noted above, wherein said process comprises:

(1) adding fatty acid soap to a reactor;

(2) combining a salt of protic acid (where acid component has a pKa lower than that of the fatty acid component of fatty acid soap) with the fatty soap at approximately 40° C. until the acid has fully reacted with the soap to generate free fatty acid and alkali metal salt of the protic acid;

(3) adding aluminate solution (which consists of a mixture of water, sodium hydroxide and alumina in certain ratios which allow all the alumina to be in solution) to react with (i.e., reverse titrate) excess free fatty acid formed upon combination of fatty acid soap and protic acid;

(4) combining with other components used to make final bar soap; and (5) cooling and finishing (e.g., optional milling, extruding, cutting and stamping, if desired).

In a third aspect of the invention, the invention relates to a method of reducing or eliminating efflorescence in a bar comprising fatty acid soap, free fatty acid, a salt of a protic acid (wherein the acid portion of protic acid salt has pKa less than that of fatty acid component of the fatty acid soap) and polyalkylene glycol (e.g., PEG) which method comprises using alkali metal aluminate solution, resulting in aluminum hydroxide in the final bar formulation (aluminate solution is used to reverse titrate excess free fatty acid formed from reaction of fatty acid soap and protic acid).

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (∀C) unless specified otherwise. All measurements are in SI units unless specified otherwise. All documents cited are—in relevant part—incorporated herein by reference.

DETAILED DESCRIPTION OF THE INVENTION

The present invention relates to a novel process for incorporating salts of certain organic protic acids (e.g., citric acids incorporated in process resulting in salts of citrate in the bar); and polyalkylene glycols and/or mixture of polyalkylene glycols into a soap-based bar while minimizing salt efflorescence associated with previous methods of incorporating free fatty acid into a soap bar. The invention also relates to novel compositions incorporating a novel combination of ingredients which result from the novel process of forming.

In one embodiment, the invention relates to bar compositions comprising:

(1) 25 to 85% by wt. free fatty acid soap (and up to 10% additional optional surfactant);

(2) 0 to 15%, preferably 1 to 10% by wt., $C_8$ to $C_{20}$ free fatty acid (formed in situ from soap component (1) although some small amount may be added separately);

(3) 0.01 to 7% by wt. protic acid salt (preferably citric acid salts), wherein the protic acid portion of the salt has a pKa less than that of the fatty acid component of the fatty acid soap;

(4) 0.2 to 8% by wt. aluminum hydroxide (resulting from aluminate solution back titrating free fatty acid to soap);

(5) about 5 to 20% water; and (6) 2 to 8% by wt. polyalkylene glycol (e.g., polyethylene glycol).

wherein said composition results in little or no efflorescence measured via storage stability testing after four weeks.

The composition of the invention is described in more detail below.

Fatty Acid Soaps

Bars made by the process of the invention comprise about 25% to 85%, preferably about 30% to 75% fatty acid soap. It is these soaps which will be "stripped" of their salt (e.g., alkali metal counterion) to become free fatty acid when salt of protic acid is used.

The term "soap" is used herein in its popular sense, i.e., the alkali metal or alkanol ammonium salts of aliphatic, alkane-, or alkene monocarboxylic acids. Sodium, potassium, magnesium, mono-, di- and tri-ethanol ammonium cations, or combinations thereof, are suitable for purposes of this invention. In general, sodium soaps are used in the compositions of this invention, but from about 1% to about 25% of the soap may be potassium or magnesium soaps. The soaps useful herein are the well known alkali metal salts of natural of synthetic aliphatic (alkanoic or alkenoic) acids having about 8 to 22 carbon atoms, preferably about 8 to about 18 carbon atoms. They may be described as alkali metal carboxylates of acrylic hydrocarbons having about 8 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives, may provide the upper end of the broad molecular weight range.

It is preferred to use soaps having the fatty acid distribution of coconut oil or tallow, or mixtures thereof, since these are among the more readily available fats. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principle chain lengths are C16 and higher. Preferred soap for use in the compositions of this invention has at least about 85% fatty acids having about 12 to 18 carbon atoms.

Coconut oil employed for the soap may be substituted in whole or in part by other "high-lauric" oils, that is, oils or fats wherein at least 50% of the total fatty acids are composed of lauric or myristic acids and mixtures thereof. These oils are generally exemplified by the tropical nut oils of the coconut oil class. For instance, they include: palm kernel oil, babassu oil, ouricuri oil, tucum oil, cohune nut oil, murumuru oil, jaboty kernel oil, khakan kernel oil, dika nut oil, and ucuhuba butter.

A preferred soap is a mixture of about 30% to about 40% coconut oil and about 60% to about 70% tallow. Mixtures may also contain higher amounts of tallow, for example, 15% to 20% coconut and 80 to 85% tallow.

The soaps may contain unsaturation in accordance with commercially acceptable standards. Excessive unsaturation is normally avoided.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric (C12), myristic (C14), palmitic (C16), or stearic (C18) acids with an alkali metal hydroxide or carbonate.

Fatty acid soap should comprise 25 to 85% by wt., preferably 30 to 75%, more preferably 50 to 75% by wt. of final composition.

Fatty Acid

A second component of the bars of the invention is free fatty acid. Free fatty acid is present in the composition and is primarily formed when the protic acid is added. If enough alkali metal aluminate solution is added during the process to make the bar, however, most or all of the free fatty acid produced when the protic acid reacts with the counterion of the fatty acid soap can be back titrated into soap. Thus, while free fatty acid very well can be, and likely will be, a part of the composition, it is not required.

As indicated and will be discussed further in connection with the process aspect of this invention, one important element of the invention is that the free fatty acid does not have to be "added on" as a separate component. Adding on free fatty acid can be much more expensive than generating the free fatty acid from soap (using the protic acid salts of the invention). However, the generation of free fatty acid (using for example protic acid) does form protic acid salt which in turn causes the bar to have efflorescence, especially in the presence of other water soluble ingredients such as, for example, polyethylene glycols. While one helpful approach or solution may be to only partially generate free fatty acid (i.e., using less protic acid than would cause the efflorescence problem) and then partially adding on some free fatty acid, it still involves the expense of adding on some free fatty acid.

According to the subject invention, the free fatty acid is instead preferably generated from soap. The efflorescence problem is remedied by creating free fatty acid in excess and than using aluminate solution (comprising water, alkali metal hydroxide and alumina to reverse titrate the fatty acid to form alkali metal soap and, for example, aluminum hydroxide. The aluminum hydroxide formed from the reverse titration has been found to mitigate or eliminate efflorescence caused by use of the salt of protic acid (e.g., citric acid, adipic acid) which was used to generate the free fatty acid from the soap in the first place.

Thus, the amount of FFA found in the final bar is from about 0 to 15% (e.g., 0%, if fully reverse titrated), preferably 0.5 to 10%, more preferably 1 to 7.5% by wt.

Free Fatty Acid

Another required component of the final bar composition is a salt of a protic acid (e.g., the salt formed as free fatty acid is generated from the alkali metal soap from the soap). A protic acid commonly is any acid that readily yields protons, i.e., a Bronstead Acid. More specifically, the protic acid salt should have pKa1 (referring to the first proton to be donated) which is less than (i.e., is typically more acidic) that of the fatty acid component of the fatty acid soap, preferably less than 6, more preferably less than 5.5. Such low pKa defines molecules which will "abstract" salt from the fatty acid soap and yield free fatty acid from the original soap.

Among the salts of such protic acids are selected specific organic acids. The selected organic protic acid salts include the magnesium, potassium and especially sodium salts of adipic acid, citric acid, glycolic acid, acetic acid, formic acid, fumaric acid, lactic acid, malic acid, maleic acid, succinic acid, and tartaric acid and polyacrylic acid. It should be remembered that, in the process, the acid form is used and that the salts are formed only after extracting counterion from the fatty acid soaps.

Especially preferred salts of organic protic acid are sodium citrate, sodium lactate, and sodium adipate.

The salt will generally comprise about 0.01 to 7.0%, preferably 0.05 to 6.0% by wt. of the final bar. Preferably the molar equivalents ratio of free fatty acid to protic acid salt is preferably between 0.5:1 to 3:1.

Alkali Metal Hydroxide (e.g., Aluminum Hydroxide)

The alkali metal hydroxide (e.g., aluminum hydroxide) in the final bar composition is generally generated when aluminate solution (comprising water, alkali metal hydroxide and alumina) in reverse titrate free fatty acid (generated when the protic acid is "extracting" the counterion from the fatty acid soap) to fatty acid soap.

Generally, the fatty acid (e.g., created as noted above or by straight addition) reacts with aluminum containing alkaline material, e.g., sodium aluminate. This may be an aluminate, for example, such as described in U.S. Pat. No. 6,207,636 to Benjamin et al. (e.g., a sodium aluminate with a solid content of 20 to 55%, preferably 30 to 55% wherein $Al_2O_3$ to $Na_2O$ is in a ratio of 0.5 to 1.55:1, preferably 1.0 to 1.5:1), the contents of which are hereby incorporated by reference into the subject application.

Whether generated as noted or even separately added, the combination of salt of protic acid and aluminum hydroxide in a final bar are believed to be novel.

The hydroxide will comprise 0.2% to 8%, preferably 0.5 to 2.5% by wt. of final bar composition.

Bars of the invention generally comprise 5 to 20%, preferably 6 to 18%, more preferably 6 to 15% water.

Finally, bars of the invention comprise about 2 to 8% polyalkylene glycol. In the absence of aluminum hydroxide (generated from use of aluminate solution as noted above), such alkylene glycols can greatly enhance effloresce. With the hydroxide, as noted, effloresce is strongly diminished and/or eliminated.

Optional

Although bars made by process of the invention are primarily fatty acid soap bars, some small percentage (e.g., 10% and below, preferably 0.01–5%) of auxiliary surfactant may be synthetic surfactant. This includes anionic surfactants, nonionic surfactants, amphoteric/zwitterionic surfactants, cationic surfactants, etc. such as are well known to the person skilled in the art. Among the many surfactants which may be used are those described in U.S. Pat. No. 3,723,325 to Parran Jr. et al. "Surface Active Agents and Detergents (Vol. I & II) by Schwartz, Perry and Berch, both of which are incorporated by reference into the subject application.

Examples of suitable anionic surfactants useful as auxiliary surfactants include: alkane and alkene sulfonates, alkyl sulfates, acyl isethionates, such as sodium cocoyl isethionate, alkyl glycerol ether sulfonates, fatty amidoethanolamide sulfosuccinates, alkyl citrates, and acyl taurates, alkyl sarcosinates, and alkyl amino carboxylates. Preferred alkyl or alkenyl groups have C12–18 chain lengths.

Examples of suitable nonionic surfactants include: ethoxylates (6–25 moles ethylene oxide) of long chain (12–22 carbon atoms) alcohol (ether ethoxylates) and fatty acids (ester ethoxylates); alkyl polyhydroxy amides such as alkyl glucamides; and alkyl polyglycosides.

Examples of suitable amphoteric surfactants include simple alkyl betaines, amido betaines, especially alkyl amidopropyl betaines, sulfo betaines, and alkyl amphoacetates.

Additives such as dyes, perfumes, soda ash, sodium chloride or other electrolyte, brighteners, etc. are normally used in an amount 0 to 3%, preferably 0.01 to 2% of the composition. Some examples are set forth below.

Perfumes; sequestering agents, such as tetrasodium ethylene diaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

In addition, the bar compositions of the invention may include 0 to 25% by wt., preferably 1 to 25% by wt., more preferably 5 to 20% by wt. skin protection and benefit agents and/or performance enhancers optional ingredients as follows:

Such optional additives may further include starches and various water soluble polymers chemically modified with hydrophobic moiety (e.g., EO-PO block copolymer); modified starches and maltodextrin.

Other optional additives may include one or more of structurants such as soluble alkaline silicate, kaolin, talc, calcium carbonate, inorganic electrolytes such as tetra sodium pyrophosphate, organic salts such as sodium citrate, sodium acetate, and modified starches.

Another class of optional ingredients are antimicrobials such as but not limited to the following:

2-hydroxy-4,2',4'-trichlorodiphenylether (DP300);
2,6-dimethyl-4-hydroxychlorobenzene (PCMX);
3,4,4'-trichlorocarbanilide (TCC);
3-trifluoromethyl-4.4'-dichlorocarbanilide (TFC);
2,2'-dihydroxy-3,3',5.5',6,6'-hexachlorodiphenylmethane;
2,2'-dihydroxy-3,3',5,5'-tetrachlorodiphenylmethane;
2,2'-dihydroxy-3,3',dibromo-5,5'-dichlorodiphenylmethane;
2-hydroxy-4,4'-dichlorodiphenylether;
2-hydroxy-3,5',4-tribromodiphenylether; and
1-hydroxyl-4-methyl-6-(2,4,4-trimethylpentyl)-2(1H)-pyridine (Octopirox).

Other suitable antimicrobials include:

Benzalkonium chloride;
Benzethonium chloride;
Carbolic acid;
Cloflucarbon (Irgasan CF3:4,4'-dichloro-3-(trifluoromethyl) carbanilide);
Chlorhexidine (CHX: 1,6-di(4'-chlorophenyl-diguanido) hexane);
Cresylic acid;
Hexetidine (5-amino-1,3-bis(2-ethylhexyl)-5-methyl-hexahydropyrimidine);
Iodophors;
Methylbenzethonium chloride;
Povidone-iodine;
Tetramethylthiuram disulfide (TMTD: Thiram);
Tribrominated salicylanilide.

Additional antimicrobials include tea tree oil, zinc salts, any of the above noted antimicrobials and mixtures thereof.

The compositions may also comprise preservatives such as dimethyloldimethylhydantoin (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic polymers as conditioners which may be used include Quatrisoft LM-200 Polyquaternium-24, Merquat Plus 3330-Polyquaternium 39; and Jaguar® type conditioners.

Polyethylene glycols as conditioners which may be used (in addition to required polyalkylene glycol) include:

| | | |
|---|---|---|
| Polyox | WSR-205 | PEG 14M, |
| Polyox | WSR-N-60K | PEG 45M, or |
| Polyox | WSR-N-750 | PEG 7M. |

Another ingredient which may be included are exfoliant particles such as polyoxyethylene beads, walnut shells, apricot seeds, and silica.

Benefit Agent

The benefit agent optionals of the subject invention may be a single benefit agent component, or it may be a benefit agent compound added via a carrier into the process stream. Further the benefit agent may be a mixture of two or more compounds, one or all of which may have a beneficial aspect. In addition, the benefit agent itself may act as a carrier for other components one may wish to add to the bar composition.

The benefit agents can be emollients, moisturizers, anti-aging agents, skin-toning agents, skin lightening agents, sun screens etc.

The preferred list of benefit agents include:

(a) silicone oils, gums and modifications thereof such as linear and cyclic polydimethylsiloxanes; amino, alkyl alkylaryl and aryl silicone oils;
(b) fats and oils including natural fats and oils such as jojoba, soybean, sunflower seed oil, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin and derivatives thereof;

(d) hydrophobic plant extracts;

(e) hydrocarbons such as liquid paraffins, petrolatum, vaseline, microcrystalline wax, ceresin, squalene, pristan, paraffin wax and mineral oil;

(f) higher fatty acids such as behenic, oleic, linoleic, linolenic, lanolic, isostearic and poly unsaturated fatty acids (PUFA);

(g) higher alcohols such as lauryl, cetyl, stearyl, oleyl, behenyl, cholesterol and 2-hexydecanol alcohol;

(h) esters such as cetyl octanoate, myristyl lactate, cetyl lactate, isopropyl myristate, myristyl myristate, isopropyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(i) essential oils such as *mentha*, jasmine, camphor, white cedar, bitter orange peel, ryu, turpentine, cinnamon, bergamot, *citrus unshiu*, calamus, pine, lavender, bay, clove, hiba, *eucalyptus*, lemon, starflower, thyme, peppermint, rose, sage, menthol, cineole, eugenol, citral, citronelle, borneol, linalool, geraniol, evening primrose, camphor, thymol, spirantol, penene, limonene and terpenoid oils;

(j) lipids such as cholesterol, ceramides, sucrose esters and pseudo-ceramides as described in European Patent Specification No. 556,957;

(k) vitamins such as vitamin A and E, and vitamin alkyl esters, including those vitamin C alkyl esters;

(l) sunscreens such as octyl methoxyl cinnamate (Parsol MCX) octocrylene(2-ethylhexyl 2-cyano-3,3-diphenylacrylate), octyl salicylate (2 ethylhexyl salicylate), benzophenone-3 (2-hydroxy-4-methoxy benzophenone), and avobenzone (4-tert-butyl-4'-methoxydibenzoylmethane) (these are merely illustrative);

(m) phospholipids; and (n) mixtures of any of the foregoing components.

A particularly preferred benefit agent is silicone, preferably silicones having viscosity greater than about 50,000 centipoise. One example is polydimethylsiloxane having viscosity of about 60,000 centistokes.

Another preferred benefit agent is benzyl laurate.

When the benefit agent is a is an oil, especially a low viscosity oil, it may be advantageous to pre-thicken it to enhance its delivery. In such cases, hydrophobic polymers of the type described in U.S. Pat. No. 5,817,609 to He et al may be employed which is incorporated by reference into the subject application.

The benefit agent generally comprises about 0–25% by wt. of the composition, preferably 5–20%, and most preferably between 2 and 10%.

The bars of the invention have little or no efflorescence. This is observed visually by the absence of visual crystalline deposits such that the bar has a smooth appearance.

Process

In a second aspect of the invention, the invention is directed to a process for making compositions noted above of the invention wherein said process comprises:

(1) adding fatty acid soap to a reactor;

(2) combining a protic acid (e.g., about 0.01 to 7% by wt.), wherein acid has pKa lower than that of the fatty acid component of fatty acid, with the fatty soap to generate free fatty acid;

(3) adding aluminate solution to react with (i.e., reverse titrate) any excess free fatty acid formed from combination of fatty acid soap and protic acid;

(4) combining with other bar components; and (5) cooling and finishing.

Conditions can be from ambient to 65° C., preferably about 35–45° C. Typically some mixing is done to blend the ingredients and allow the reaction to occur.

Efflorescence

The bars of the invention are characterized in that they show no significant sign of efflorescence, by which is meant no visual crystalline formation. The bars thus have a “smooth” appearance.

Testing is done by placing naked bars on racks in ovens set to 30° C. and 70% relative humidity. Samples are checked once a week.

Samples are tested after 4 weeks to determine if there are any visual signs of efflorescence.

Except in the operating and comparative examples, or where otherwise explicitly indicated, all numbers in this description indicating amounts or ratios of materials or conditions or reaction, physical properties of materials and/or use are to be understood as modified by the word “about”.

Where used in the specification, the term “comprising” is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

EXAMPLES

Examples 1–4

In order to show how bars having components of the invention and prepared by process of the invention are effective in stopping efflorescence, applicants prepared Comparatives Bars A & B and Bars 1 & 2 as noted in Table 1 below:

TABLE 1

| | A-Citric Acid | B-Coconut Fatty Acid (No Efflorescence) | 1 | 2 |
|---|---|---|---|---|
| Free Fatty Acid (FFA) via citric acid | 5.50% | 3.50% | 5.50% | 5.50% |
| FFA to react with aluminate | | | (5) | (10) |
| Alumina | | | 1.10% | 2.20% |
| Sodium Citrate | 1.99% | 1.27% | 3.80% | 5.61% |
| Hardened CNFA (coconut fatty acid) | | 2.00% | | |
| Perfume | 1.15% | 1.15% | 1.15% | 1.15% |
| TiO2 | 0.50% | 0.50% | 0.50% | 0.50% |
| Target moisture (water) | 13.50% | 13.50% | 13.50% | 13.50% |
| PEG 600 | 4.00% | 4.00% | 4.00% | 4.00% |
| Silicone DC 200 1000 cps | 1.00% | 1.00% | 1.00% | 1.00% |
| Anhydrous Soap | 74.35% | 73.08% | 69.45% | 66.54% |

Comparative A (where no aluminate solution is used) showed efflorescence readily. Comparative B (also with no aluminate) has no efflorescence, but only because FFA is added separately (e.g., is not formed from a reaction which generates excessive salt during formation of free fatty acid). Rather, free fatty acid was added separately. There is no hydroxide because, as noted, no aluminate solution was needed to reverse titrate free fatty acid formed from soap. This process, however, is very expensive and limited to how much free fatty acid can be added.

Examples 1 and 2, by contrast, were made as per the invention. That is, free fatty acid was generated from fatty acid soap (rather than added separately as in Example B) by the addition of citric acid; aluminate solution was used to reverse titrate the thus generated free fatty acid back to soap and hydroxide was generated from this reverse titration. The parenthesis for second row numbers (i.e., FFA to react with aluminate) represents excess FFA which was made which was then reverse titrated into soap as noted.

Bars 1 and 2 did not have FFA added on top and did not show efflorescence under the storage conditions defined for test.

What is claimed is:

1. A process for making bar composition comprising:

(1) 25 to 85% by wt. fatty acid soap;

(2) 1 to 15% $C_8$ to $C_{20}$ free fatty acid;

(3) 0.01 to 7% protic acid salt, wherein protic acid has pKa less than that of the fatty acid component of the fatty acid soap;

(4) 0.2 to 20% by wt. aluminum hydroxide;

(5) 2 to 8% polyalkylene glycol; and (6) 5 to 20%% by wt. water; wherein said composition results in little or no efflorescence measured after 4 weeks of storage at about 35–45° C. and 70% relative humidity.

wherein said process comprises:

(i) adding fatty acid soap to a reactor;

(ii) combining protic acid having a pKa lower than that of fatty acid component of said fatty acid with said fatty acid soap at about 40° C. to generate free fatty acid and alkali metal salt of said protic acid, and wherein said free fatty acid of (2) is generated from the fatty acid soap of (1);

(iii) adding aluminate solution comprising water, alkali metal hydroxide and aluminate; and (iv) adding other component of soap bar solution, wherein steps (i) to (iv) may be interchangeable combined in any order of addition; and (v) cooling ingredients mixed in steps (i) to (iv) followed by formation and diminishing of bar composition.

2. A process according to claim 1, wherein said composition additionally comprises 0.1 to 10% surfactant.

3. A process according to claim 1, wherein said composition comprises 0.5 to 10% by wt. free fatty acid.

4. A process according to claim 1, wherein in said composition, said protic acid salt is an organic salt selected from the group consisting of alkali metal salt of adipic acid, citric acid, glycolic acid, acetic acid, formic acid, fumaric acid, lactic acid, malic acid, maleic acid, succinic acid, and tartaric acid and polyacrylic acid and mixtures thereof.

5. A process composition according to claim 4, comprises alkali metal citrate.

6. A process according to claim 1, comprising 0.05 to 6% protic acid salt.

7. A process according to claim 1, comprising 0.1 to 8% aluminum.

8. A process according to claim 1, wherein said finishing comprises extruding, cutting and stamping final bar.

9. A process according to claim 1, wherein said finishing comprises melt casting final bar.

* * * * *